(12) United States Patent
Cunningham

(10) Patent No.: US 6,990,259 B2
(45) Date of Patent: Jan. 24, 2006

(54) PHOTONIC CRYSTAL DEFECT CAVITY BIOSENSOR

(75) Inventor: Brian T. Cunningham, Lexington, MA (US)

(73) Assignee: SRU Biosystems, Inc., Woburn, MA (US)

( * ) Notice: Subject to any disclaimer, the term of this patent is extended or adjusted under 35 U.S.C. 154(b) by 120 days.

(21) Appl. No.: 10/812,635

(22) Filed: Mar. 29, 2004

(65) Prior Publication Data

US 2005/0213868 A1 Sep. 29, 2005

(51) Int. Cl.
G02B 6/00 (2006.01)

(52) U.S. Cl. .................................... 385/12; 435/288.7

(58) Field of Classification Search ................. 385/12; 435/288.7
See application file for complete search history.

(56) References Cited

U.S. PATENT DOCUMENTS

| | | | |
|---|---|---|---|
| 2002/0127565 A1 | 9/2002 | Cunningham et al. | 435/6 |
| 2003/0017580 A1 | 1/2003 | Cunningham et al. | 435/287.2 |
| 2003/0017581 A1 | 1/2003 | Li et al. | 435/287.2 |
| 2003/0026891 A1 | 2/2003 | Qiu et al. | 427/58 |
| 2003/0027327 A1 | 2/2003 | Cunningham et al. | 435/287.2 |
| 2003/0027328 A1 | 2/2003 | Cunningham et al. | 435/287.2 |
| 2003/0032039 A1 | 2/2003 | Cunningham et al. | 435/6 |
| 2003/0059855 A1 | 3/2003 | Cunningham et al. | 435/7.9 |
| 2003/0068657 A1 | 4/2003 | Lin et al. | 435/7.9 |
| 2003/0077660 A1 | 4/2003 | Pien et al. | 435/7.1 |
| 2003/0092075 A1 | 5/2003 | Pepper | 435/7.9 |
| 2003/0113766 A1 | 6/2003 | Pepper et al. | 435/6 |
| 2005/0200942 A1 * | 9/2005 | Grot et al. | 359/321 |

OTHER PUBLICATIONS

Pacradouni, V., W.J.Mandeville, A.R. Cowan, P. Paddon, J.F. Young, and S.R. Johnson, *Photonic band structure of dielectric membranes periodically textured in two dimensions*, Physical Review B, 2000 62(7): p. 4204-4207.

Yablonovitc, E. *Inhibited spontaneous emission in solid-state physics and electronicds*, Physical Review Letters, 1987. 58(20); p. 2059-2062.

Quang, T.., M. Woldeyohannes, s. John, and G.S. Agarwal, *Coherent control of spontaneous emission*, Physical Review Letters, 1997. 79(26);p. 5238-5241.

Liu, Z., S. Tibuleac, D. Shin, P.P. Young, and R. Magnusson, *High efficiency guided-mode resonance filter*. Optics Letters, 1998. 2319): p. 1556-1558.

Neviere, M., P.Vincent, R. Petit., and M. Cadilhac, *Systematic study of resonances of holographic thin film couplers*. Optics Communications, 1973. 9(1): p. 48-52.

Magnusson, R., and S.S. Wang, *New principle for optical filters*, Applied Physics Letters, 1992. 61(9): p. 1022-1024.

Magnusson, R., and S.S. Wang, *Transmission bandpass guided-mode resonance filters*. Applied Optics, 1995. 34 (35): p. 8106-8109.

Peng, S. *Experimental demonstration of resonant anomalies in diffraction from two-dimensional gratings*. Optics Letters, G. Michael Morris. 21(8): p. 549-551.

Wang, S.S. and R. Magnusson, *Theory and applications of guided-mode resonance filters*. Applied Optics, 1993. 32 (14): p. 2606-2613.

(Continued)

*Primary Examiner*—Sarah Song
(74) *Attorney, Agent, or Firm*—McDonnell Boehnen Hulbert & Berghoff LLP

(57) ABSTRACT

A biosensor is described having the form of a photonic crystal having defect cavities formed in a periodic pattern in the device. The invention provides a higher sensitivity and a greater degree of spatial localization of incoupled photons than previously reported photonic crystal biosensor devices.

19 Claims, 10 Drawing Sheets

OTHER PUBLICATIONS

Wang, S.S., R. Magnusson, J.S. Bagby, and M.G. Moharam, *Guided-mode resonance in planar dielectric-layer diffraction gratings*. J. Optical Society of America A, 1990.7(8): p. 1470-1474.

Tibuleac, S. and R. Magnusson, *Diffractive narrow-band transmission filters based on guided-mode resonance effects in thin-film multilayers*. IEEE Photonics Technology Letters, 1997.9(4): p. 464-466.

Cunningham, B. T., P. Li, B. Lin, and J. Pepper, *Colorimetric resonant reflection as a direct biochemical assay technique*. Sensors and Actuators B, 2002.81: p. 316-328.

Cunningham, B.T., J. Qiu, P. Li, J. Pepper, and B. Hugh, *Aplastic colorimetric resonant optical biosensor for multi parallel detection of label-free biochemical interactions*. Sensors and Actuators B, 2002.85: p. 219-226.

Haes, A.J. and R.P.V. Duyne, *A Nanoscale Optical Biosensor: Sensitivity and Selectivity of an Approach Based on the Localized Surface Plasmon Resonance Spectrosocopy of Triangular Silver Nanoparticles*. Journal of the American Chemical Society, 2002.124, p. 10596-10604.

Li, P., B. Lin, J. Gerstenmaier, and B. T. Cunningham, *A new method for a label-free imaging of biomolecular interactions*. Sensors and Actuators B, 2003.

John, S., *Strong localization of photons in certain disordered dielectric superlattices*. Physical Review Letters, 1987.58 (23): p. 2486-2489.

Srinvasan, K., P.E. Barclay, o. Painter, J. Chen, A.Y. Cho, and C. Gmachi, *Experimental demonstration of a high quality factor photonic crystal microcavity*. Applied Physics Letters, 2003.83(10): p. 1915-1917.

Painter, O., K. Srinivasan, J.D. O'Brien, A. Scherer, and P.D. Dapkus, *Tailoring of the resonant mode properties of optical nanocavities in two-dimensional photonic crystal slab waveguides*. JQ\1cflla 1 of Optics A: Pure and Applied Optics, 2001.3: p. S161-S170.

John, S. and V.1. Rupasov, *Multiphoton localization and propagating quantum gap solutions in a frequency gap medium*. Physical Review Letters, 1997.79(5): p. 821-824.

Altug, H. and J. Vuckovic, *Two-dimensional coupled photonic crystal resonator arrays*. Applied Physics Letters, 2004. 84(2): p. 161-163.

A. Scherer, T. Yoshie, M. Lončar, J. Vučković, K. Okamoto, *Photonic Crystal Nanocavities for Efficient Light Confinement and Emission*, Journal of the Korean Physical Society, vol. 42, Supp. 2, pp. 768-773, 2003.

* cited by examiner

PHOTONIC CRYSTAL DEFECT CAVITY BIOSENSOR

BACKGROUND OF THE INVENTION

A. Field of the Invention

This invention relates generally to photonic crystal biochemical sensor devices. Such devices are used for optical detection of the adsorption of a biological material, such as DNA, protein, viruses or cells, or chemicals, onto a surface of the device or within a volume of the device. More particularly, this invention is related to a biosensor having the form of a photonic crystal having defect cavities formed in a periodic pattern in the device. The invention provides a higher sensitivity and a greater degree of spatial localization of incoupled photons than previously reported photonic crystal biosensor devices.

B. Description of Related Art

Photonic Crystals

Photonic crystals represent a new class of optical devices that have been enabled by recent advances in semiconductor fabrication tools with the ability to accurately deposit and etch materials with precision less than 100 nm. Photonic crystals are characterized by an infinite or semi-infinite periodic structure containing alternating materials of low dielectric permittivity and high dielectric permittivity. In principle, a photonic crystal structure may extend in 1, 2, or 3 dimensions of space. For background information on photonic crystals, the reader is directed to Joannopoulos, J. D., R. D. Meade, and J. N. Winn, *Photonic Crystals*, 1995 Princeton, N.J.: Princeton University Press.

Along with the development of appropriate fabrication methods, accurate computer modeling tools are also becoming available which facilitate design of components with the ability to manipulate the propagation of light within a photonic crystal structure. Like the periodic arrangement of atoms within a semiconductor crystal that results in the formation of energy bands which dictate the conduction properties of electrons, the periodic arrangement of macroscopic dielectric media within a photonic crystal is designed to control the propagation of electromagnetic waves. Because the period of the structure is smaller than the wavelength of light, such devices are often referred to as "sub-wavelength surfaces" or as "nanostructured surfaces" because typical dimensions are 50–300 nm. Using photonic crystal design principles, one may construct devices with optical energy bands, which effectively prevent the propagation of light in specified directions and energies, while allowing concentration of electromagnetic field intensity within desired volumes and surfaces. See, e.g., Munk, B. A., *Frequency Selective Surfaces*. Wiley Interscience. 2000: John Wiley & Sons; Pacradouni, V., W. J. Mandeville, A. R. Cowan, P. Paddon, J. F. Young, and S. R. Johnson, *Photonic band structure of dielectric membranes periodically textured in two dimensions*. Physical Review B, 2000. 62(7): p. 4204–4207.

The applications of photonic crystal structures within the field of optoelectronics have been numerous, including integration with lasers to inhibit or enhance spontaneous emission, waveguide angle steering devices, and narrowband optical filters. See e.g. Quang, T., M. Woldeyohannes, S. John, and G. S. Agarwal, *Coherent control of spontaneous emission*. Physical Review Letters, 1997. 79(26): p. 5238–5241 Liu, Z. S., S. Tibuleac, D. Shin, P. P. Young, and R. Magnusson, *High efficiency guided-mode resonance filter*. Optics Letters, 1998. 23(19): p. 1556–1558; Peng, S., *Experimental demonstration of resonant anomalies in diffraction from two-dimensional gratings*. Optics Letters, G. Michael Morris. 21(8): p. 549–551; Magnusson, R. and S. S. Wang, *New principle for optical filters*. Applied Physics Letters, 1992. 61(9): p. 1022–1024. Several device applications take advantage of the photonic crystal structure geometry's capability for concentrating light into extremely small volumes with very high local electromagnetic field intensity.

Defect cavity photonic crystals have been widely reported in the literature for their ability to enhance the Q and to spatially localize regions of high electromagnetic field intensity. John, S., *Strong localization of photons in certain disordered dielectric superlattices*. Physical Review Letters, 1987. 58(23): p. 2486–2489; Scherer, A., T. Yoshie, M. Loncar, J. Vuckovic, K. Okamoto, and D. Deppe, *Photonic crystal nanocavities for efficient light confinement and emission*. Journal of the Korean Physical Society, 2003. 42: p. 768–773; Srinivasan, K., P. E. Barclay, O. Painter, J. Chen, A. Y. Cho, and C. Gmachi, *Experimental demonstration of a high quality factor photonic crystal microcavity*. Applied Physics Letters, 2003. 83(10): p. 1915–1917; Painter, O., K. Srinivasan, J. D. O'Brien, A. Scherer, and P. D. Dapkus, *Tailoring of the resonant mode properties of optical nanocavities in two-dimensional photonic crystal slab waveguides*. Journal of Optics A: Pure and Applied Optics, 2001. 3: p. S161–S170 and John, S. and V. I. Rupasov, *Multiphoton localization and propagating quantum gap solitons in a frequency gap medium*. Physical Review Letters, 1997. 79(5): p. 821–824. Periodic arrays of defect cavities in a photonic crystal are reported in Altug, H. and J. Vuckovic, *Two-dimensional coupled photonic crystal resonator arrays*. Applied Physics Letters, 2004. 84(2): p. 161–163.

Photonic Crystal Biosensors

Several properties of photonic crystals make them ideal candidates for application as optical biosensors. First, the reflectance/transmittance behavior of a photonic crystal can be readily manipulated by the adsorption of biological material such as proteins, DNA, cells, virus particles, and bacteria. Each of these types of material has demonstrated the ability to alter the optical path length of light passing through them by virtue of their finite dielectric permittivity. Second, the reflected/transmitted spectra of photonic crystals can be extremely narrow, enabling high-resolution determination of shifts in their optical properties due to biochemical binding while using simple illumination and detection apparatus. Third, photonic crystal structures can be designed to highly localize electromagnetic field propagation, so that a single photonic crystal surface can be used to support, in parallel, the measurement of a large number of biochemical binding events without optical interference between neighboring regions within <3–5 microns. Finally, a wide range of materials and fabrication methods can be employed to build practical photonic crystal devices with high surface/volume ratios, and the capability for concentrating the electromagnetic field intensity in regions in contact with a biochemical test sample. The materials and fabrication methods can be selected to optimize high-volume manufacturing using plastic-based materials or high-sensitivity performance using semiconductor materials.

Representative examples of biosensors in the prior art are disclosed in Cunningham, B. T., P. Li, B. Lin, and J. Pepper, *Colorimetric resonant reflection as a direct biochemical assay technique*. Sensors and Actuators B, 2002. 81: p. 316–328; Cunningham, B. T., J. Qiu, P. Li, J. Pepper, and B. Hugh, *A plastic calorimetric resonant optical biosensor for multiparallel detection of label-free biochemical interactions*, Sensors and Actuators B, 2002. 85: p. 219–226; Haes, A. J. and R. P. V. Duyne, *A Nanoscale Optical Biosensor: Sensitivity and Selectivity of an Approach Based on the Localized Surface Plasmon Resonance Spectroscopy of Triangular Silver Nanoparticles.* Journal of the American Chemical Society, 2002. 124: p. 10596–10604.

The combined advantages of photonic crystal biosensors may not be exceeded by any other label-free biosensor technique. The development of highly sensitive, miniature, low cost, highly parallel biosensors and simple, miniature, and rugged readout instrumentation will enable biosensors to be applied in the fields of pharmaceutical discovery, diagnostic testing, environmental testing, and food safety in applications that have not been economically feasible in the past.

In order to adapt a photonic bandgap device to perform as a biosensor, some portion of the structure must be in contact with a liquid test sample. Biomolecules, cells, proteins, or other substances are introduced to the portion of the photonic crystal and adsorbed where the locally confined electromagnetic field intensity is greatest. As a result, the resonant coupling of light into the crystal is modified, and the reflected/transmitted output (i.e., peak wavelength) is tuned, i.e., shifted. The amount of shift in the reflected output is related to the amount of substance present on the sensor. The sensors are used in conjunction with an illumination and detection instrument that directs polarized light into the sensor and captures the reflected or transmitted light. The reflected or transmitted light is fed to a spectrometer that measures the shift in the peak wavelength.

The ability of photonic crystals to provide high quality factor (Q) resonant light coupling, high electromagnetic energy density, and tight optical confinement can also be exploited to produce highly sensitive biochemical sensors. Here, Q is a measure of the sharpness of the peak wavelength at the resonant frequency. Photonic crystal biosensors are designed to allow a liquid test sample to penetrate the periodic lattice, and to tune the resonant optical coupling condition through modification of the surface dielectric constant of the crystal through the attachment of biomolecules or cells. Due to the high Q of the resonance, and the strong interaction of coupled electromagnetic fields with surface-bound materials, several of the highest sensitivity biosensor devices reported are derived from photonic crystals. See the Cunningham et al. papers cited previously. Such devices have demonstrated the capability for detecting molecules with molecular weights less than 200 Daltons (Da) with high signal-to-noise margins, and for detecting individual cells. Because resonantly-coupled light within a photonic crystal can be effectively spatially confined, a photonic crystal surface is capable of supporting large numbers of simultaneous biochemical assays in an array format, where neighboring regions within ~10 $\mu$m of each other can be measured independently. See Li, P., B. Lin, J. Gerstenmaier, and B. T. Cunningham, *A new method for label-free imaging of biomolecular interactions.* Sensors and Actuators B, 2003.

There are many practical benefits for biosensors based on photonic crystal structures. Direct detection of biochemical and cellular binding without the use of a fluorophore, radioligand or secondary reporter removes experimental uncertainty induced by the effect of the label on molecular conformation, blocking of active binding epitopes, steric hindrance, inaccessibility of the labeling site, or the inability to find an appropriate label that functions equivalently for all molecules in an experiment. Label-free detection methods greatly simplify the time and effort required for assay development, while removing experimental artifacts from quenching, shelf life, and background fluorescence. Compared to other label-free optical biosensors, photonic crystals are easily queried by simply illuminating at normal incidence with a broadband light source (such as a light bulb or LED) and measuring shifts in the reflected color. The simple excitation/readout scheme enables low cost, miniature, robust systems that are suitable for use in laboratory instruments as well as portable handheld systems for point-of-care medical diagnostics and environmental monitoring. Because the photonic crystal itself consumes no power, the devices are easily embedded within a variety of liquid or gas sampling systems, or deployed in the context of an optical network where a single illumination/detection base station can track the status of thousands of sensors within a building. While photonic crystal biosensors can be fabricated using a wide variety of materials and methods, high sensitivity structures have been demonstrated using plastic-based processes that can be performed on continuous sheets of film. Plastic-based designs and manufacturing methods will enable photonic crystal biosensors to be used in applications where low cost/assay is required, that have not been previously economically feasible for other optical biosensors.

The assignee of the present invention has developed a first generation photonic crystal biosensor and associated detection instrument. The sensor and detection instrument are described in the patent literature; see U.S. patent application publications U.S. 2003/0027327; 2002/0127565, 2003/0059855 and 2003/0032039. Methods for detection of a shift in the resonant peak wavelength are taught in U.S. Patent application publication 2003/0077660. The biosensor described in these references include 1- and 2-dimensional periodic structured surfaces produced on continuous sheets of plastic film. The crystal resonant wavelength is determined by measuring the peak reflectivity at normal incidence with a spectrometer to obtain a wavelength resolution of 0.5 picometer. The resulting mass detection sensitivity of <1 pg/mm$^2$ (obtained without 3-dimensional hydrogel surface chemistry) has not been demonstrated by any other commercially available biosensor.

A fundamental advantage of first-generation photonic crystal biosensor devices is their ability to be mass-manufactured with plastic materials in continuous processes at a 1–2 feet/minute rate. Methods of mass production of the sensors are disclosed in U.S. Patent application publication 2003/0017581. As shown in FIG. 1, the periodic surface structure of a biosensor 10 is fabricated from a low refractive index material 12 that is overcoated with a thin film of higher refractive index material 14. The low refractive index material 12 is bonded to a substrate 16. The surface structure is replicated within a layer of cured epoxy 12 from a silicon-wafer "master" mold (i.e. a negative of the desired replicated structure) using a continuous-film process on a polyester substrate 16. The liquid epoxy 12 conforms to the shape of the master grating, and is subsequently cured by exposure to ultraviolet light. The cured epoxy 12 preferentially adheres to the polyester substrate sheet 16, and is peeled away from the silicon wafer. Sensor fabrication was completed by sputter deposition of 120 nm titanium oxide (TiO$_2$) high index of refraction material 14 on the cured epoxy 12 grating surface. Following titanium oxide deposition, 3×5-inch microplate sections were cut from the sensor sheet, and attached to the bottoms of bottomless 96-well and 384-well microtiter plates with epoxy.

As shown in FIG. 2, the wells 20 defining the wells of the microtiter plate contain a liquid sample 22. The combination of the bottomless microplate and the biosensor structure 10 is collectively shown as biosensor apparatus 26. Using this approach, photonic crystal sensors are mass produced on a square-yardage basis at very low cost.

The first-generation detection instrument for the photonic crystal biosensor is simple, inexpensive, low power, and robust. A schematic diagram of the system is shown in FIG. 2. In order to detect the reflected resonance, a white light source illuminates a ~1 mm diameter region of the sensor surface through a 100 micrometer diameter fiber optic 32 and a collimating lens 34 at nominally normal incidence through the bottom of the microplate. A detection fiber 36 is bundled with the illumination fiber 32 for gathering reflected light for analysis with a spectrometer 38. A series of 8 illumination/detection heads 40 are arranged in a linear fashion, so that reflection spectra are gathered from all 8 wells in a microplate column at once. See FIG. 3. The microplate+biosensor 10 sits upon a X-Y addressable motion stage (not shown in FIG. 2) so that each column of wells in the microplate can be addressed in sequence. The instrument measures all 96 wells in ~15 seconds, limited by the rate of the motion stage. Further details on the construction of the system of FIGS. 2 and 3 are set forth in the published U.S. patent application Ser. No. 2003/0059855.

SUMMARY OF THE INVENTION

The present invention provides further improvements and advancements to the photonic crystal and colorimetric biosensors known in the prior art. Rather than using a regular repeating periodic structure to design a structured surface for a photonic crystal biosensor, as disclosed in the above-referenced patent application publications, the present invention provides for a photonic crystal biosensor in the form of an array of unit cells. Defects in the periodic structure of the sensor are introduced. The defects are introduced intentionally in the sensor design, typically one per unit cell, and consist of regions where the local dielectric permittivity is higher than the surrounding regions of the surface structure. The defects result in locally (around the defect) concentrated regions of high electromagnetic field density, compared to the regions away from the defect. The use of defects within a photonic crystal biosensor has not been previously reported.

More particularly, a defect cavity photonic crystal biosensor is provided which consists of an array of two-dimensional unit cells, each of the unit cells having a substrate and a multitude of raised portions arranged in a regular repeating pattern wherein the raised portions are separated from each other by adjacent void portions. The raised portions are made from a material having a relatively high index of refraction n1 greater than that of water. Each of the unit cells further comprises comprise a defect wherein the regular repeating pattern of the raised portions separated by adjacent voids is modified such that, at the defect, the material having a relatively high index of refraction n1 occupies the space which would otherwise been occupied by one or more of the voids. The defect is such that a localized maximum of electromagnetic field intensity is produced in the region of the defect in response to incident light on said photonic crystal at a resonant frequency. During use, a fluid containing a sample to be tested is placed on the photonic crystal and contained in or absorbed in the void portions surrounding the defect.

In preferred embodiments, a sample retaining structure is placed adjacent to the array having a plurality of openings in registry with a plurality of the unit cells, wherein a biological or chemical sample may be introduced into the openings in the structure and adsorbed by the array proximate to the defect cavities of the unit cells. An example of such a sample retaining structure is the microtitre plates described previously.

The advantage over prior art biosensors without defect cavities as disclosed herein is potentially higher sensitivity, through higher interaction of the surface electromagnetic field and the test sample, better detection system resolution through more narrow resonant peaks that can be tracked with higher fidelity, and higher spatial resolution by potentially limiting incoupled photon lateral propagation distance to less than 3 microns.

This invention is a significant advance in the art because it allows for the development of label-free biosensor detection systems capable of detecting analytes with lower molecular weight, lower biochemical binding affinity, and lower concentration than would otherwise be possible. Sensors made in accordance with the illustrated embodiments provide both sharper resonant peaks (higher Q), and greater local concentration of electromagnetic field energy in the region of the defect cavities, which help produce a sensor with greater sensitivity. The higher sensitivity methods enabled by this invention are highly desired in commercial applications such as pharmaceutical screening, diagnostic tests, and environmental monitoring systems.

DETAILED DESCRIPTION OF THE PREFERRED EMBODIMENT

Figure 5A:
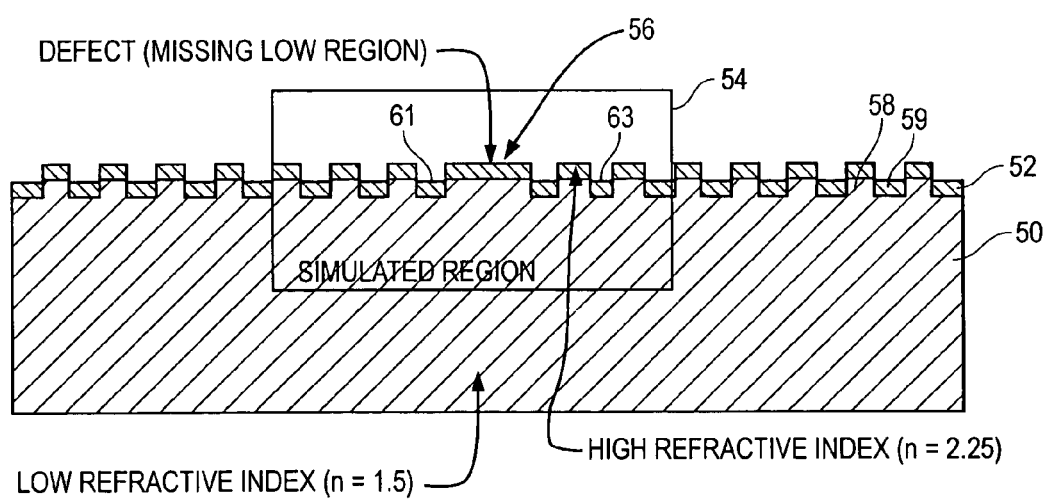
FIG. 5A is a cross-section of a unit cell of a two dimensional photonic crystal biosensor with a defect in the center of the unit cell.

A photonic crystal biosensor is described herein which has defect cavities to improve the Q factor and sensitivity of the sensor. Examples of such biosensors will be described below in conjunction with the examples of FIGS. 5A, 6A and 7. The sensor is formed as an array of two-dimensional unit cells, each of the unit cells having a substrate and a multitude of raised portions arranged in a regular repeating pattern wherein the raised portions are separated from each other by adjacent void portions. The raised portions are made from a material having a relatively high index of refraction n1 greater than that of water. In one possible embodiment the high index of refraction material 52 is sputter deposited onto the substrate pattern of raised portions 58 and adjacent void or low regions 59, as shown in FIG. 5A.

Each of the unit cells includes a defect wherein the regular repeating pattern of raised portions separated by adjacent voids is modified such that, at the defect, the material having a relatively high index of refraction n1 occupies the space of one or more of the voids. This can be seen for example in FIG. 5A in which the defect 56 comprises a missing void or low region at the center of the unit cell (three consecutive raised portions in a regular square wave pattern of raised portions and adjacent void portions).

Figure 5B:
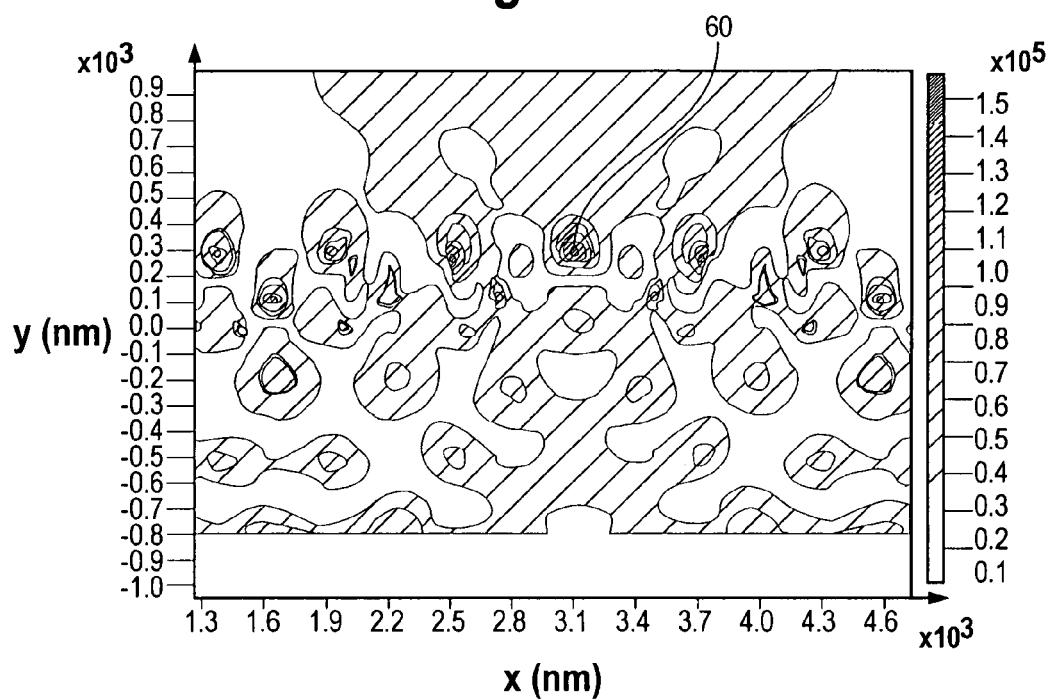
FIG. 5B is a two-dimensional plot of electromagnetic field intensity in the X and Y directions for the unit cell of FIG. 5A, obtained by using an FDTD computer model of the unit cell.
Figure 6A:
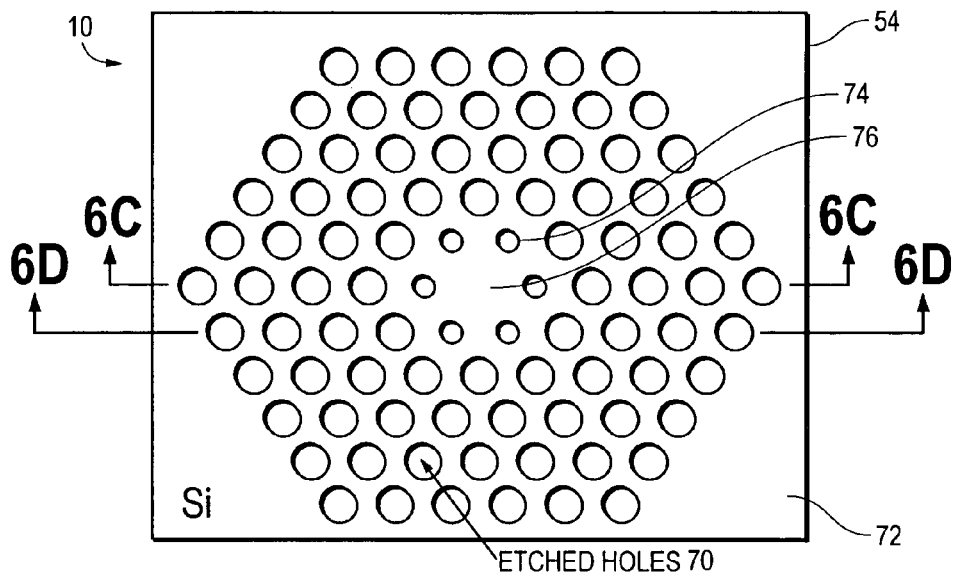
FIG. 6A is a plan view of a unit cell of an alternative arrangement of a defect cavity photonic crystal biosensor.
Figure 6B:
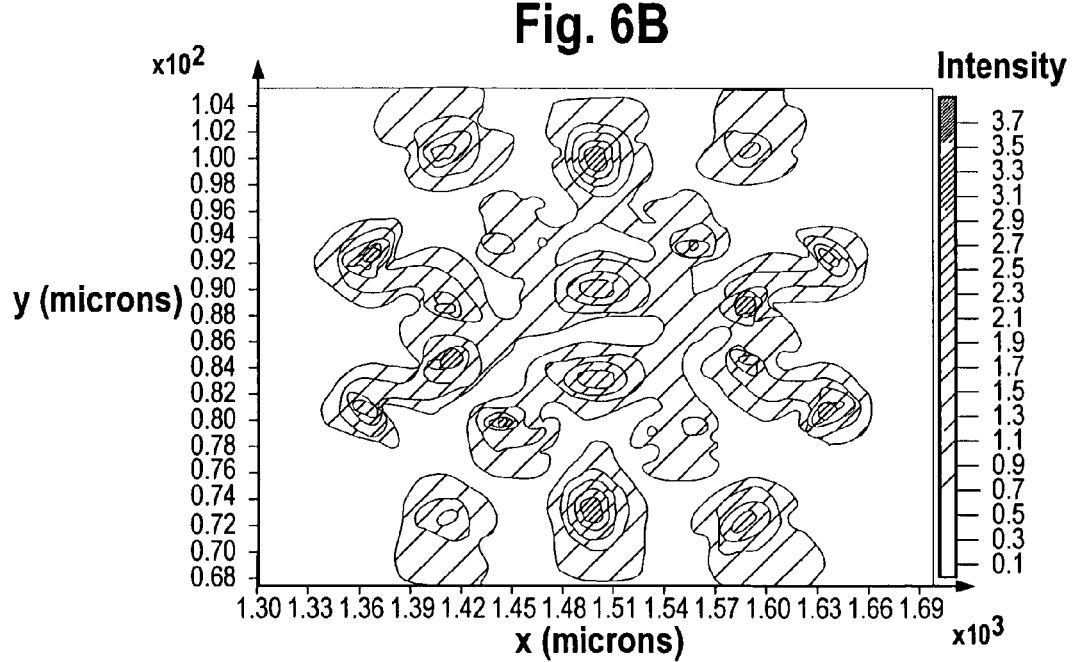
FIG. 6B is a two-dimensional plot of electromagnetic field intensity in the X and Y directions for the unit cell of FIG. 6A, obtained by using an FDTD computer model of the unit cell.

A localized maximum of electromagnetic field intensity is produced in the region of the defect in response to incident light on the photonic crystal at a resonant frequency. This property is shown in FIGS. 5B and 6B and discussed further below.

During use, a fluid containing a sample to be tested is placed on the photonic crystal and contained in the void portions in the space immediately above the surface of the sensor. A detection apparatus such as shown in FIG. 2, 3 or 8–11 detects the shift in the peak wavelength value at the resonant frequency due to the change in the index of refraction in the medium directly above the surface of the sensor. The shift in peak wavelength value provides information as to the contents of the sample due to the change in index of refraction, as reported in the literature cited in the background section.

Thus, in a principle aspect of this invention, resonant cavities within a photonic crystal lattice are formed from intentionally-introduced local defect regions, where the dielectric permittivity of the defect is higher than that of the surrounding non-defect region. Defect cavities may be introduced through the omission of a hole in a 2D lattice (e.g., as shown in FIG. 5A), the omission of a line in a 1D lattice, or in a tapered lattice duty cycle. FIG. 6A shows one possible embodiment of a defect 76 in the center of a hexagonal arrangement of holes 70 formed in a Si substrate, in which the holes at the center is omitted, and the holes 74 surrounding the center are smaller than those further away from the center. Other configurations for a defect cavity photonic crystal biosensor are of course possible.

Optical microcavities are typically characterized by two key quantities, the quality factor (Q), a measure of the photon lifetime for the optical cavity mode (computed as the change in peak wavelength value divided by the full width of the peak at half maximum), and the modal volume ($V_{eff}$), a measure of the spatial extent and energy density of the mode. While first-generation photonic crystal biosensors demonstrate Q~1000, and a lateral photon propagation distance of ~3–5 µm, defect cavity structures have been demonstrated using computer modeling with Q~40,000, and cavity confinement approaching the theoretical limit of one half wavelength. For a photonic crystal biosensor, an increase in Q results in a decreased width of the reflected resonance spectrum, which, in turn, results in the ability to resolve smaller shifts in the resonant wavelength. In addition, a limitation of the photon lateral propagation distance to ~500 nm would enable ~10x improved spatial resolution for binding images to be obtained. Improved spatial resolution can be used to increase microarray density to a scale where 10 µm diameter microarray spots can be effectively imaged. The ability to measure binding from a 500×500 nm spot, as enabled by this invention, also has important implications in that it leads directly to assay miniaturization. Micro/nanofluidic control systems are under development which will have the capability for dispensing reagents with sub-nanoliter volumes and sub-micrometer precision. The use of such control systems, combined with miniaturized assays, leads to the ability to test or screen a large number of samples in a short amount of time using the apparatus of FIGS. 8–11 or a modification thereof.

In order to take advantage of defect cavity structures for photonic crystal biosensors, a periodic array of defect cavities is preferably produced in an array that covers an entire biosensor surface (such as a bottomless 3×5-inch microplate or 1×3-inch microarray bonded to the surface of the sensor). Further information on periodic arrays of defect cavities are found in Altug, H. and J. Vuckovic, *Two-dimensional coupled photonic crystal resonator arrays*. Applied Physics Letters, 2004. 84(2): p. 161–163 Finite-difference-time-domain (FDTD) computer modeling methods are preferably used to design and simulate the defect cavity structures in a biosensor. FDTD modeling has been shown to be an effective method for predicting resonant wavelength, resonant peak width, polarization dependence, $V_{eff}$, and sensitivity.

Example and Comparison to Non-defect Cavity Biosensors

In the course of building, measuring, and computer modeling a guided mode resonant filter (GMRF) biosensor (an example of a 1-D surface photonic crystal), for example one as described in the prior published applications cited previously, the present inventor came to more fully understand the relationship between surface electromagnetic field intensity and sensitivity to surface adsorbed biological material. In particular, a finite-difference time-domain (FDTD) computer modeling method was used which enabled the visualization of the distribution of electromagnetic fields within any device structure, and the determination of the extent of lateral propagation of incoupled photons at the resonant wavelength.

Using Finite-Difference Time-Domain (FDTD) computer analysis, the performance of a photonic crystal biosensor structure without defects (PC) was compared with a defect-cavity photonic crystal (DCPC) biosensor. FDTD is an accurate method for determining the interaction of any physical structure with electromagnetic radiation. It involves representing the physical structure to be modeled as a 2 or 3-dimensional object consisting of materials with known dielectric permittivity. The physical structure is broken down into a fine mesh of volume elements, where each volume element is described by its individual dielectric properties. The physical structure can be illuminated with brief pulses of light with any origin, orientation, polarization, and intensity. FDTD solves Maxwell's equations to determine a nearly exact representation of how the light pulse propagates through the physical structure. Because the light pulse can be represented as a Fourier transform of many separate independent sinusoidal functions, FDTD can determine the frequency (or, equivalently wavelength) transmission/reflection characteristics of the physical structure. FDTD can also determine a spatial map of the electromagnetic field strength within and around the physical structure for any electromagnetic field component and any wavelength. For physical structures such as photonic crystals with periodically repeating patterns of dielectric permittivity in one or more directions, FDTD allows simulation of only a single "unit cell" of the structure with the application of periodic boundary conditions. The results of a periodic boundary condition simulation provide an accurate determination of the field characteristics if the unit cell is assumed to extend into infinity.

In this work, a commercially available software package (available from Lumerical Solutions, Inc. Suite 405–238 Alvin Narod Mews, Vancouver British Columbia, Canada V6B 5Z3) was run on a personal computer. First, a 1-dimensional linear photonic crystal biosensor of the design described in Cunningham, B. T., J. Qiu, P. Li, J. Pepper, and B. Hugh, *A plastic colorimetric resonant optical biosensor for multiparallel detection of label-free biochemical interactions*. Sensors and Actuators B, 2002. 85: p. 219–226 was simulated. Next, the same structure was simulated with a defect cavity introduced into the structure.

Figure 1:
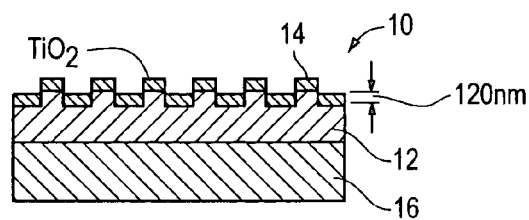
FIG. 1 is an illustration of a prior art biosensor arrangement.
Figure 2:
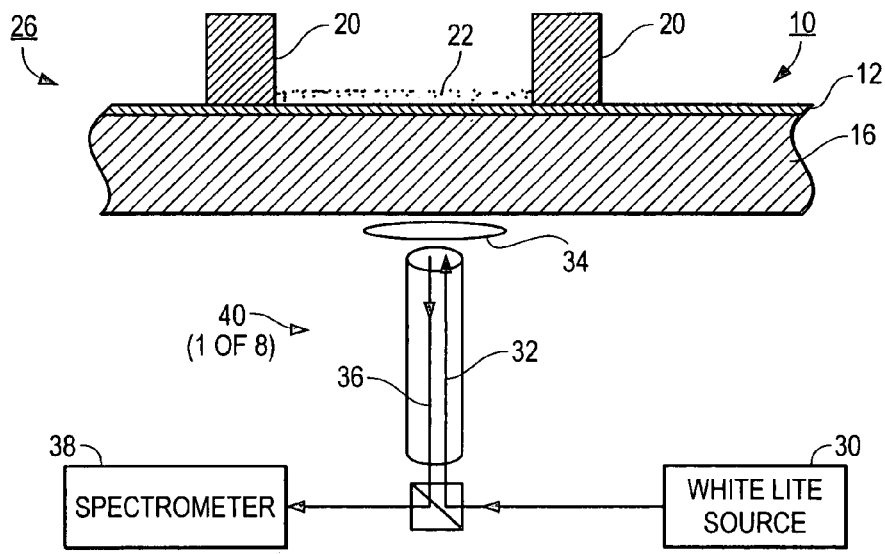
FIG. 2 is an illustration of a prior art biosensor and detection system for illuminating the biosensor and measuring shifts in the peak wavelength of reflected light from the biosensor.
Figure 4A:
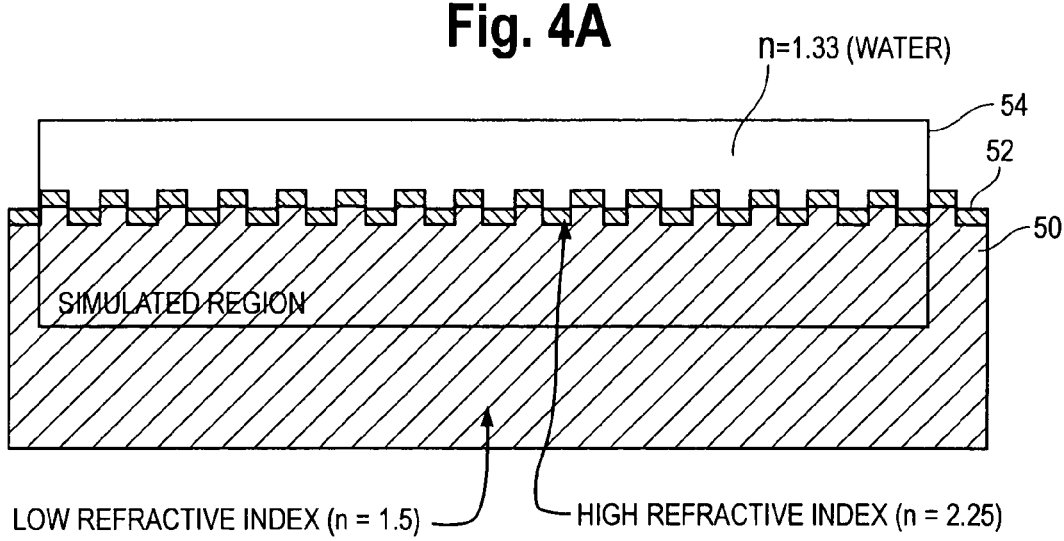
FIG. 4A is a cross-section of a unit cell of a two dimensional prior art photonic crystal biosensor.

The structure of the PC without a defect is shown in FIG. 4A. It consists of a repeating pattern of raised regions 58 and adjacent void or low regions 59 in a square wave pattern. The low refractive index (n=1.5) dielectric material 50 with a linear grating (square wave) extending into the page (z-direction), and repeating into infinity in the x-direction. The surface structure (raised portion 58) height is 170 nm. The high and low regions of the low refractive index surface structure are covered with a 120 nm-thick $TiO_2$ high refractive index material 52 (n=2.25). The period of the structure is 500 nm, with equal width high and low regions. In the FDTD model, the unit cell 54, representing 15 periods of the grating, is shown by the box in FIG. 4A. The unit cell encompasses some of the area above and below the grating structure. The mesh of the structure is divided into 25 nm increments in the x- and y-dimensions. The region above the PC structure represents a water test sample (n=1.33). The structure is illuminated from below with an infinite (in the xz plane) TE polarized 5 fsec Gaussian pulse with an intensity of 1 V/m, essentially as shown in FIG. 2.

Figure 4B:
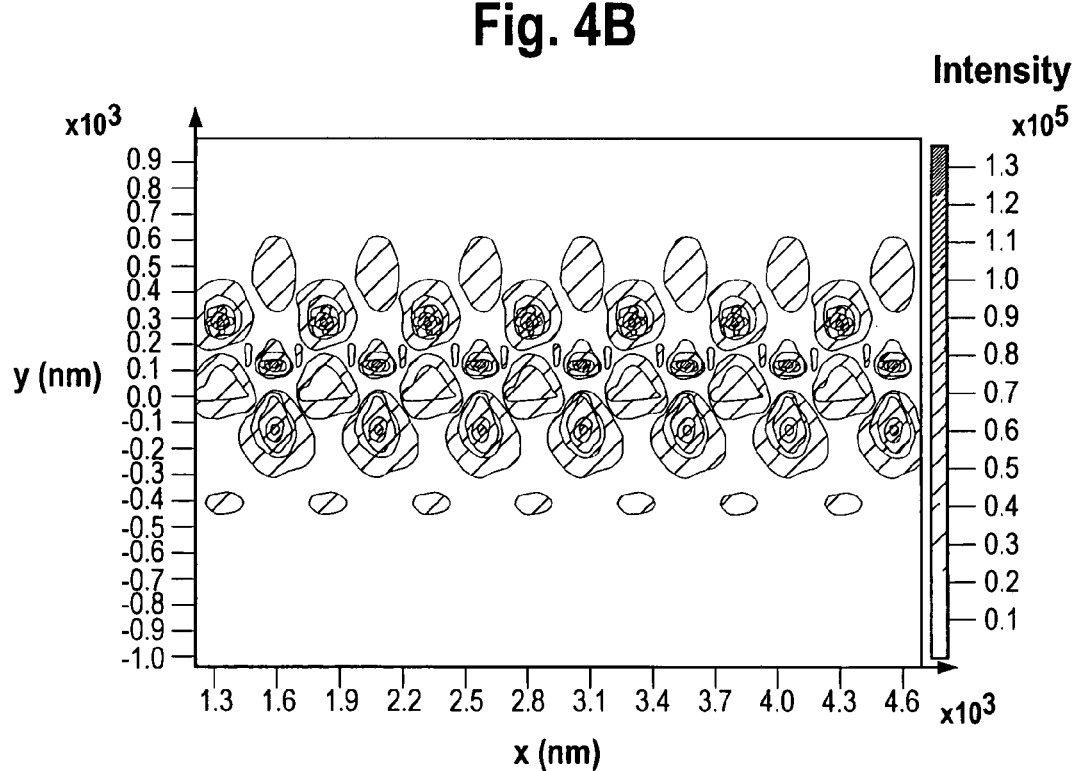
FIG. 4B is a two-dimensional plot of electromagnetic field intensity in the X and Y directions for the unit cell of FIG. 4A, obtained by using an FDTD computer model of the unit cell.
Figure 4C:
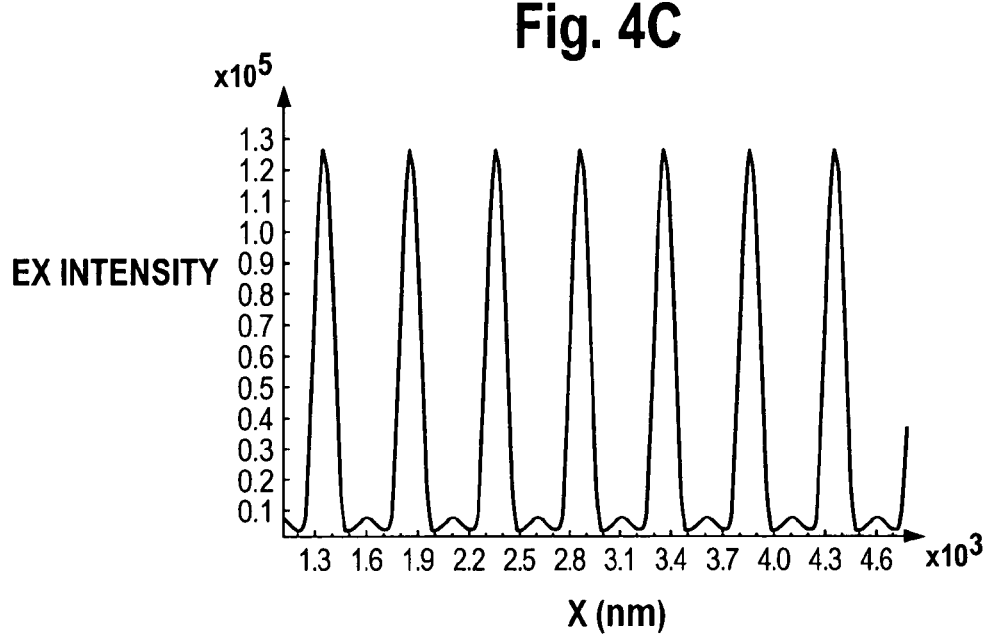
FIG. 4C is a graph of the X component of the electromagnetic field intensity for the sensor of FIG. 4A as a function of distance in the X direction, as calculated by the FDTD computer model at the top of the grating of the sensor, at the resonant frequency.
Figure 4D:
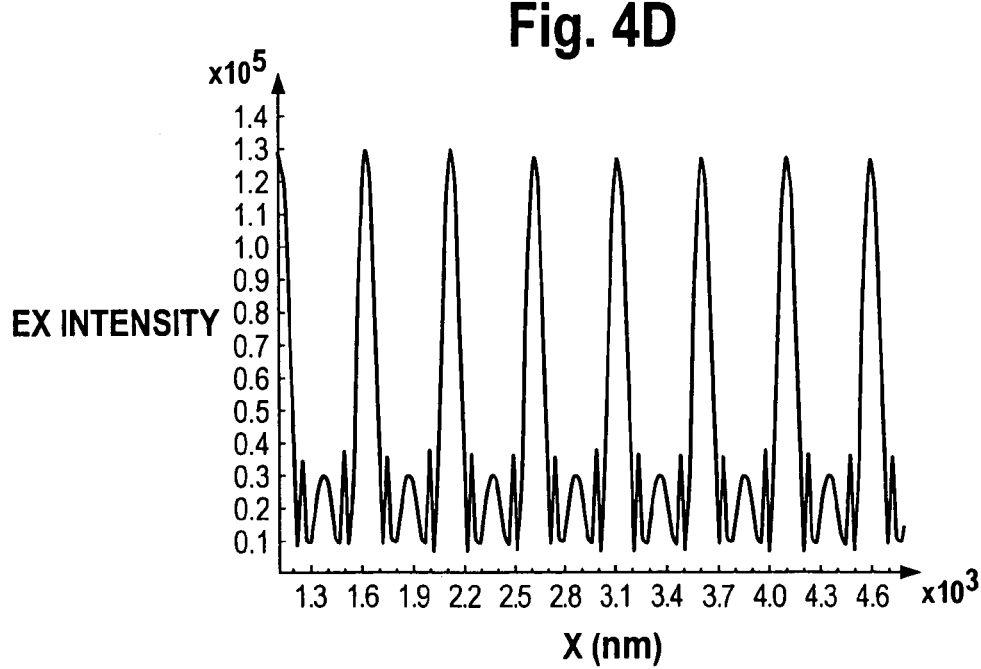
FIG. 4D is a graph of the X component of the electromagnetic field intensity for the sensor of FIG. 4A as a function of the distance in the X direction, as calculated by the FDTD computer model at the bottom of the grating of the sensor, at the resonant frequency.
Figure 4E:
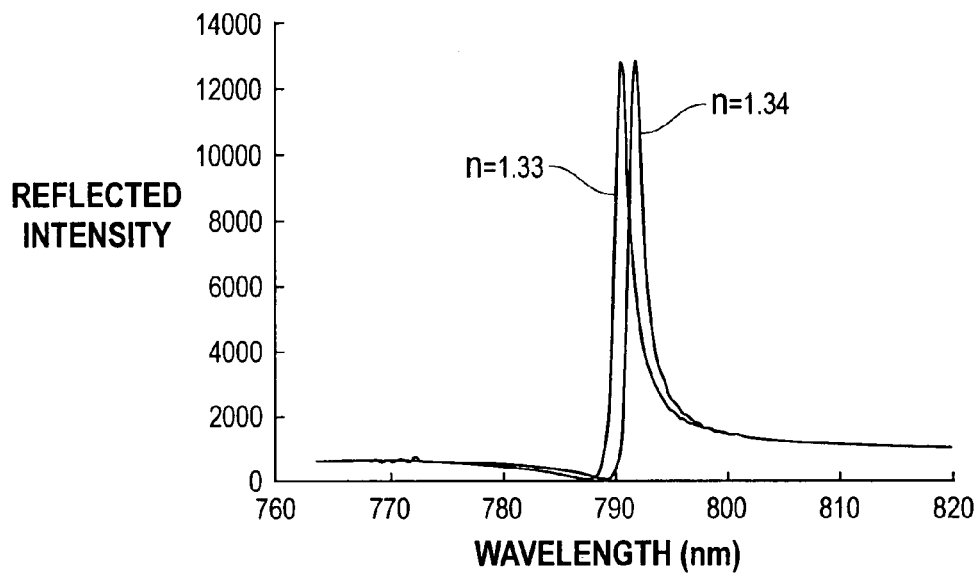
FIG. 4E is a graph of reflected intensity of electromagnetic field as a function of wavelength, showing the peak wavelength at n=1.33 for material adjacent to the biosensor (simulating water present at the void regions of the biosensor), and at n=1.34 for material adjacent to the biosensor, with the graph clearly showing a shift to the right at the peak wavelength for n=1.34.

For the PC structure, FDTD determined that the frequency for resonant coupling is 378.5 THz (790 nm wavelength). The spatial electromagnetic field distribution of the $E_x$ field component at the resonant wavelength is shown in FIG. 4B. Due to the periodic surface structure, as expected, the field intensity follows a periodic pattern, with highest field regions on the upper structure surfaces, as shown in FIG. 4C (the grating top surface is defined as the top of the square waves in FIG. 4A). FIG. 4D shows the field intensity at the grating bottom surface (at the base of the square waves in FIG. 4A). The reflected wavelength spectrum is shown in FIG. 4E (curve for n=1.33). The interaction of the sensor with the test sample is determined by repeating the simulation, but with an increased "water" refractive index of n=1.34. The higher water refractive index results in a shift of the resonant peak to a higher wavelength. A shift coefficient (ShCoe) is defined as the change in resonant wavelength divided by the change in water refractive index (ShCoe=$\Delta\lambda_p/\Delta n$). A shift coefficient of 125 is determined for this structure, and is consistent with values measured for actual PC sensors.

Next, a defect cavity photonic crystal (DCPC) structure was simulated. The DCPC structure was identical to the PC structure, except that one low region of the square wave grating was replaced by a high region, as shown in FIG. 5A at 56. Using the unit cell enclosed by the box 54, the defect is repeated every $7^{th}$ period of the PC grating, with the defect approximately at the center of the unit cell. Because the defect essentially displaces a low refractive index material (water, n=1.33) which otherwise would have been present at a void in the center 56) with a higher refractive index material (n=1.5, i.e., the raised portion in the substrate at the center 56, and n=2.25, the high index of refraction material deposited on the raised portion at 56), the defect at 56 represents a region in the crystal with a higher refractive index than the regions surrounding the defect, e.g., at 61 and 63.

Figure 5C:
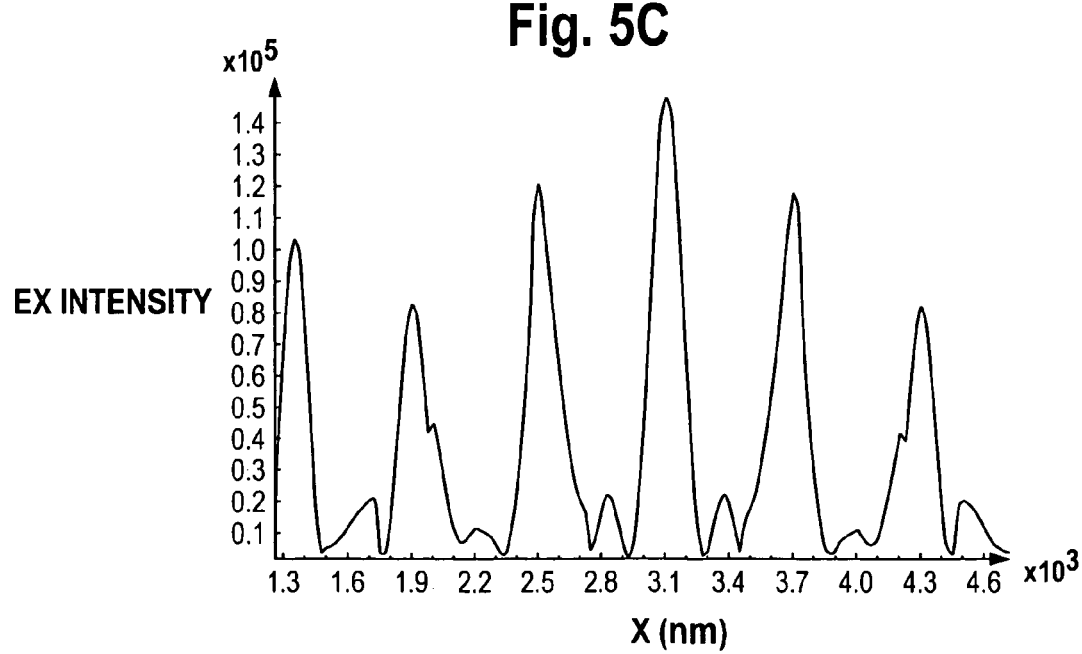
FIG. 5C is a graph of the X component of the electromagnetic field intensity for the sensor of FIG. 5A as a function of distance in the X direction, as calculated by the FDTD computer model at the top of the grating of the sensor, at the resonant frequency.
Figure 5D:
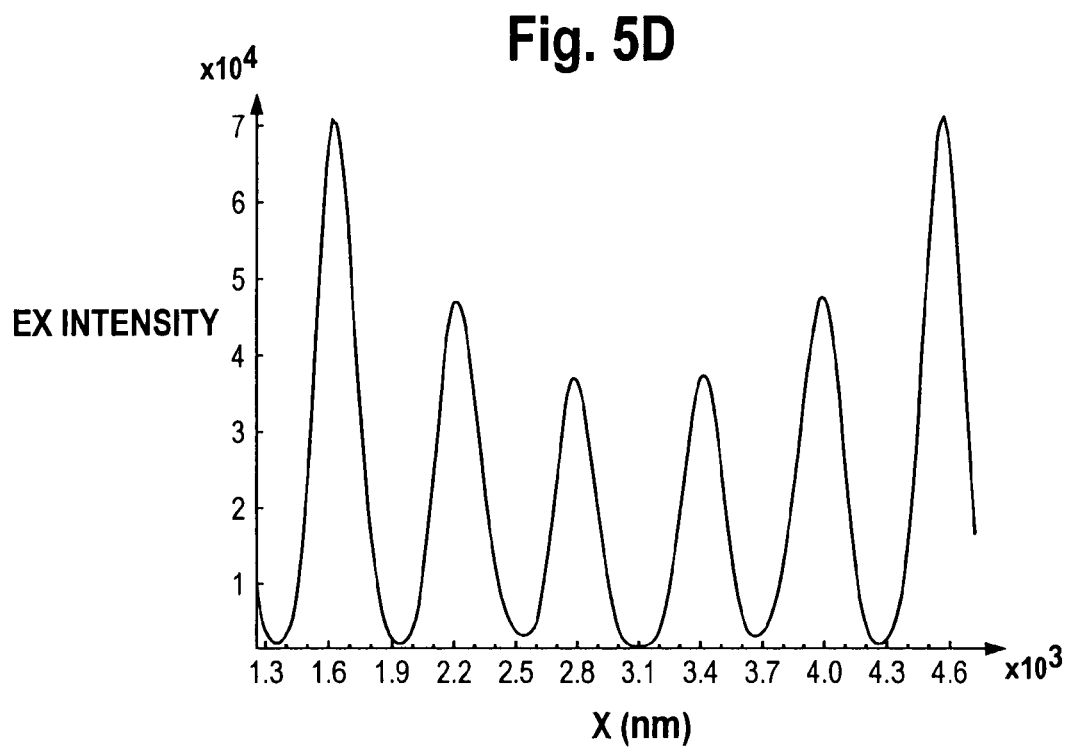
FIG. 5D is a graph of the X component of the electromagnetic field intensity for the sensor of FIG. 5A as a function of the distance in the X direction, as calculated by the FDTD computer model at the bottom of the grating of the sensor, at the resonant frequency.
Figure 5E:
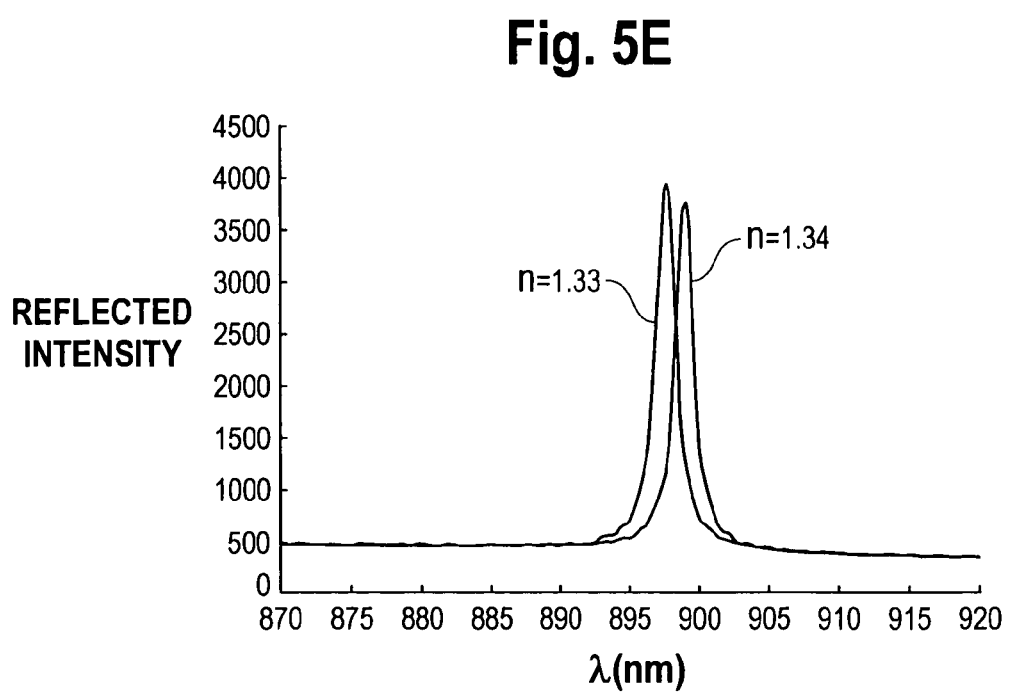
FIG. 5E is a graph of reflected intensity of electromagnetic field as a function of wavelength, showing the peak wavelength at n=1.33 for material adjacent to the biosensor (simulating water present at the void regions of the biosensor), and at n=1.34 for material adjacent to the biosensor, with the graph clearly showing a shift to the right at the peak wavelength for n=1.34.

Using the same simulation conditions that were used with the PC structure of FIG. 4A, FDTD determined a resonant frequency of 334.2 THz (897 nm wavelength). A higher resonant wavelength is expected for the defect structure, as it has a higher net dielectric permittivity than the PC structure without the defect (FIG. 4A), based on the replacement of water (n=1.33) with n=1.5 and n=2.25 material. The spatial electromagnetic field distribution of the $E_x$ field component at the resonant wavelength is shown in FIG. 5B. The distribution shows that regions of the most intense electromagnetic field are located near the defect (spot 60), and lower peak field strength is obtained away from the defect. As before, the highest field intensity is obtained on the upper and lower exposed surfaces of the structure (grating top and bottom surfaces, as defined above), as shown in FIGS. 5C and 5D. The reflectance spectrum for the sensor of FIG. 5A for n=1.33 and n=1.34 in the region directly above the surface of the grating is show in FIG. 5E. The shift coefficient of the DCPC structure of FIG. 5A was found to be 134. A 7% improvement in sensitivity to the "bulk" refractive index of the test sample is obtained by the introduction of a small defect as shown in FIG. 5A.

Other Examples of Defect Cavity Photonic Crystal Biosensors

Figure 6C:
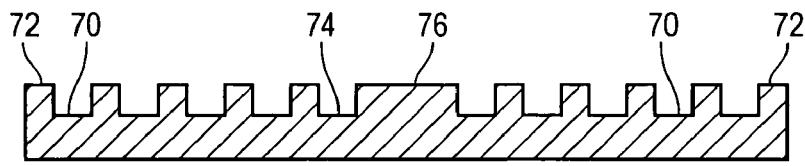
FIGS. 6C and 6D are cross-sections of the unit cell of FIG. 6A, taken along the lines 6C—6C and 6D—6D of FIG. 6A.
Figure 6D:
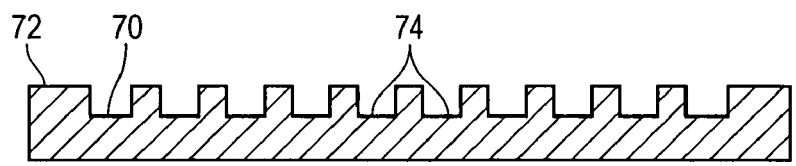

FIG. 6A is a plan view of a unit cell of an alternative arrangement of a defect cavity photonic crystal biosensor 10. The sensor 10 consists of a Si wafer substrate 72 having a multitude of unit cells arranged in a two-dimensional array, one of which is shown in FIG. 6A. The unit cell includes a defect 76 at the center of the unit cell. The pattern of raised portions and adjacent void or low regions is formed by an arrangement of holes 70 etched in the substrate 72, in which the hole which would otherwise be at the center 76 is omitted, and the holes 74 surrounding the center 76 are smaller than those further away from the center. FIGS. 6C and 6D are cross-sections of the unit cell of FIG. 6A, taken along the liens 6C—6C and 6D—6D of FIG. 6A.

FIG. 6B is a two-dimensional plot of electromagnetic field intensity in the X and Y directions for the unit cell of FIG. 6A, obtained by using an FDTD computer model of the unit cell. A defect in a photonic crystal lattice (shown here as an array of etched holes in a silicon wafer) results in localized confinement of photons in the region surrounding the defect, resulting in higher resonator Q factor, and higher local electromagnetic field intensity. An array of unit cells 54 of FIG. 6A with such defects on a photonic crystal surface are as a means for increasing resolution and sensitivity of photonic crystal biosensors.

The array of unit cells of FIG. 6A in preferred embodiments is bonded to the bottom of a microarray device which provides a means for containing a fluid sample on the surface of the sensor. The sample holding wells in the microarray has a structure, preferably one of rows and columns, and the detection instrument preferably has a plurality of illumination and detection heads to read each of the wells in parallel. It will be appreciated that in some embodiments, there will be many unit cells per well in microarray, depending on the size of the well and the size of the unit cells, but also that the wells and reading and detection instrument may be miniaturized such that there are only a few, or even one, unit cell per illumination and detection head. Also, it will be appreciated that the illumination of any of the defect cavity biosensor described herein could be from below (as shown in FIG. 2) or from above, and that the illumination could from below the substrate and the detection apparatus could be positioned above the substrate, detecting the transmission of light through the sensor.

Figure 7:
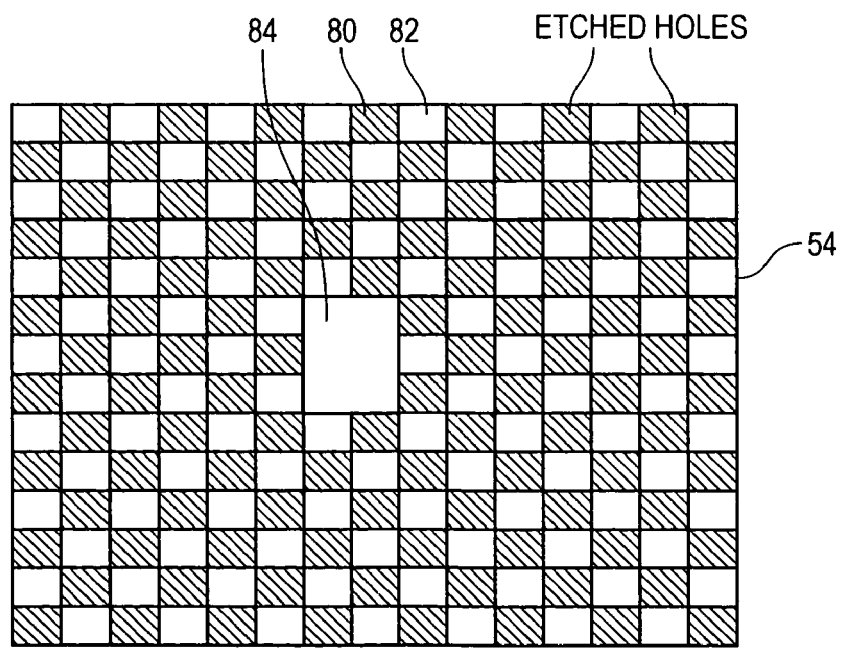
FIG. 7 is a plan view of an alternative embodiment of a defect cavity photonic crystal biosensor.

FIG. 7 shows another embodiment in which the unit cell 54 of a photonic crystal consists of a two-dimensional checkerboard pattern in which a substrate material (e.g., Si) has a repeating patter of cubic etched holes 80 and adjacent cubic raised portions 82. The height of the raised portions 82 (or, equivalently, the depth of the adjacent etched holes) could be all the same or they could have a tapered duty cycle wherein as the holes approach the center 84 of the unit cell they are progressively shallower. The center portion 84 consists of portions of the substrate in which the etched hole is omitted entirely, resulting in a region of relatively higher dielectric permittivity in the center region 84 than in the region immediately surrounding the center.

Other configurations for a defect cavity photonic crystal biosensor are of course possible. Detailed designs for other embodiments defect cavity photonic crystal biosensors are preferably arrived at using the FDTD techniques described herein.

Representative Detection Instrument

A representative detection instrument for illuminating a biosensor, detection of reflected radiation, and determining the peak wavelength at the resonant frequency is shown in FIGS. 8–11. The instrument of FIGS. 8–11 is specifically designed for use with a sensor affixed to the bottom of a bottomless microtiter plate of 8 columns of wells and 12 rows. It will be appreciated that modification of the instrument design, particularly miniaturization of critical system components, may be made for other embodiments.

The detection instrument 100 includes a plurality of dual illumination and detection fiber optic heads 40 (FIG. 2) be arranged side by side in a linear fashion. By utilizing such a linear arrangement, a plurality of dual heads can simultaneously illuminate and then read out a plurality of sensor surface locations. For example, a linear probe arrangement is utilized in the instrument 100 to illuminate and then read an entire row or an entire column of a microtiter plate. In this preferred embodiment, each dual probe head contains two optical fibers. The first fiber is connected to a white light source to cast a small spot of collimated light on the sensor surface. The second fiber reflects the reflected radiation and supplies it to a spectrometer. After one row is illuminated, relative motion occurs between the detector probes and the sensor (microtiter plate) and the next row or column of the sensor is read. The process continues until all rows (or columns) have been read.

As will be described in further detail below, in one embodiment of the measuring apparatus, a biosensor comprising the combination of bottomless microtiter plate and affixed sensor grating is placed on a linear motion stage. The linear motion stage moves the microplate in a specified, linear scan direction. As the microtiter plate is moved in this scan direction, each microplate column is sequentially illuminated. The resulting reflected light is measured. In one preferred embodiment, a scan of a conventional 96-well microtiter plate may take approximately 15 to 30 seconds to illuminate and measure the resultant reflected spectrum.

In yet another alternative embodiment, an imaging apparatus utilizes a spectrometer unit that comprises an imaging spectrometer. One advantage of the imaging spectrometer system is that such imaging systems reduce the amount of time for determining the peak wavelength value (PWv). Another advantage is to study biological binding of an area in a non-uniform fashion. The use of an imaging spectrometer is described in further detail in U.S. patent application publication 2003/0059855. The instrument includes a spectrometer unit preferably comprising an imaging spectrometer containing a two-dimensional Charge Coupled Device (CCD) camera and a diffraction grating. The reflected light containing the biosensor resonance signal for each spot is diffracted by the grating in the spectrometer unit. The diffraction produces a spatially segregated wavelength spectra for each point within the illuminated area. The wavelength spectrum has a second spatial component corresponding to the direction transverse to the scan direction. This second spatial component is subdivided into discrete portions corresponding to in this transverse direction.

For example, if the imaging spectrometer includes a CCD camera that contains 512×2048 imaging elements, then an illuminating line is spatially segregated into 512 imaging elements or points. A wavelength spectra is measured for each of the 512 imaging elements or points along the orthogonal axis of the CCD camera. Where the CCD camera contains 512×2048 imaging elements, the CCD would have a resolution of 2048 wavelength data points. Using this method, the PWV's of 512 points are determined for a single "line" or imaging area across the sensor bottom surface. For a conventional CCD imaging camera typically having spatial resolution of approximately 10 microns, a 1:1 imaging system is capable of resolving PWV values on sensor surface 342 with a 10 micron resolution. In order to measure a PWV image of the entire sensor bottom surface, the sensor is transported along an imaging plane (scan direction), and subsequent line scans are used to construct a PWV image.

Figure 3:
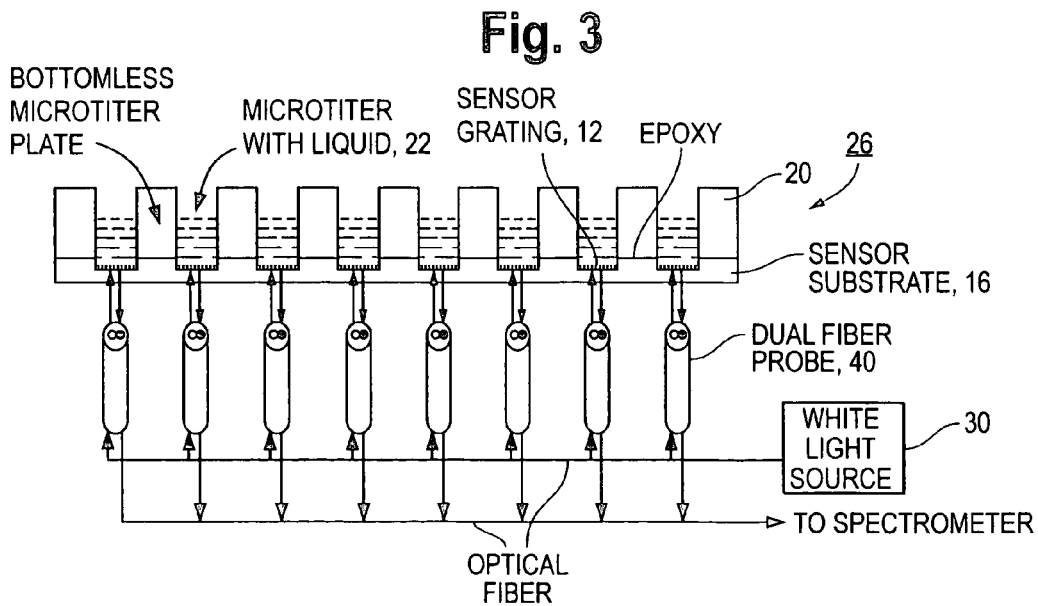
FIG. 3 is an illustration of an arrangement of 8 illumination heads that read an entire row of wells of a biosensor device comprising the structure of FIG. 1 affixed to the bottom of bottomless microtiter plate.
Figure 8:
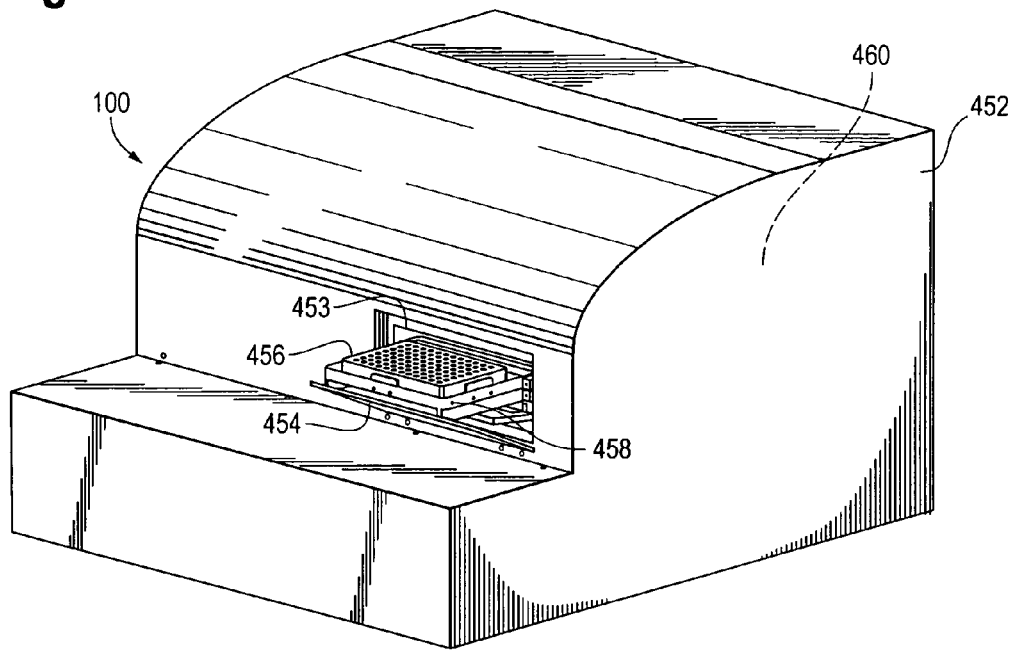
FIGS. 8–11 are various views of an instrument for illuminating the defect cavity photonic crystal biosensors and collecting the reflected light in order to determine shifts in the peak wavelength.

The embodiment of FIGS. 8–11 shows an illumination and detection instrument that incorporates the illumination and detection features of FIGS. 2 and 3. FIG. 8 illustrates a perspective view of the measuring instrument 100. The instrument 100 includes a measuring instrument cover 452 and a door 454. A microplate well plate (or microtiter plate) 456 conFigured as a biosensor in accordance with this invention is shown in an extracted position, outside an incubator assembly 460 incorporated in the interior of instrument 100. The microplate well plate 456 is held by a microwell tray 458. The tray 458 may extend out of the incubator assembly 460 through a door way 453 located at the front of the incubator assembly 460. The incubator assembly 460 allows the tray 458 to be maintained at a user defined temperature during microwell tray read out and/or measurement.

In one preferred embodiment, the incubator assembly 460 is used for performing assays at controlled temperatures, typically such controlled temperatures may range from 4 and 45 degrees Celsius. As will be explained with reference to FIGS. 9–11, a collimator assembly 708 is positioned preferably beneath a bottom portion 602 of the incubator assembly 460. During microtiter well illumination and wavelength measurement, the collimator assembly 708 illuminates a bottom surface 459 of the tray 458.

Figure 9:
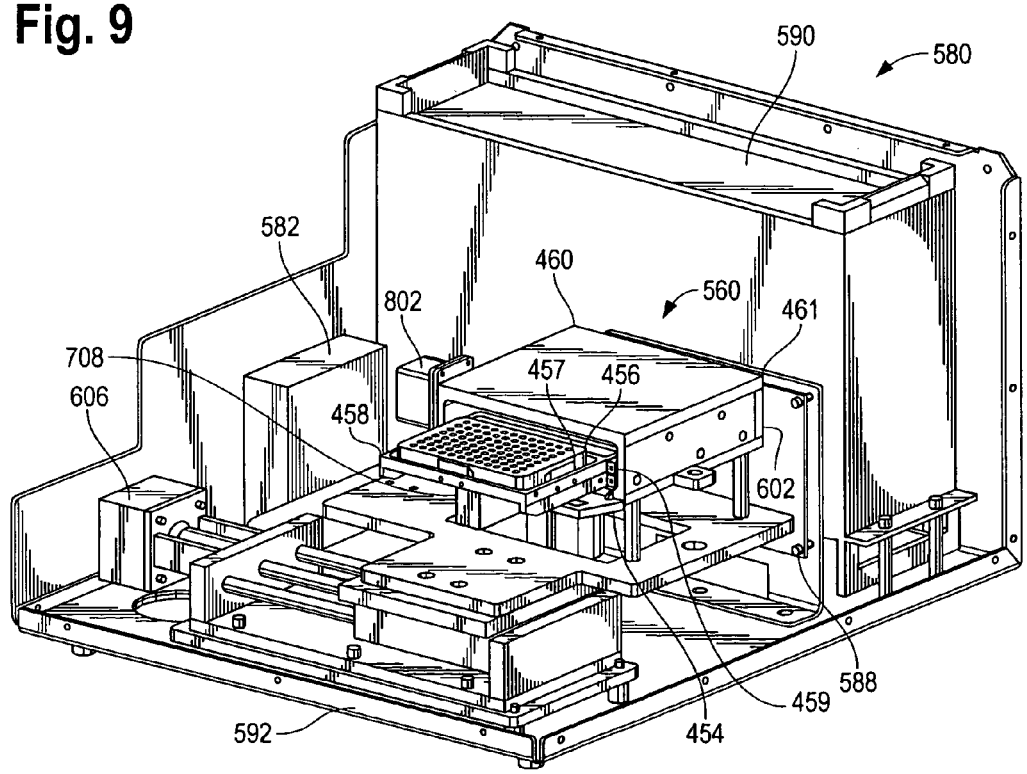

While the tray 458 remains in an extracted position outside of the incubator assembly 460, the microtiter plate 456 may be placed on or removed from the tray 458. The plate 456 may be held in the tray 458 via a set of registration points, spring clips, or other known types of securing means. In FIG. 9, clips 457 are used to hold the plate 456 in the tray 458.

After the microtiter plate 456 has been loaded with a fluid sample with biological material to be detected and measured, the tray 458 is transported into the incubator assembly 460. Processing, mixing, heating, and/or readout of the biosensors may then begin, preferably under the control of a electronic microprocessor controller (not shown) on a controller board 588 (see FIG. 9).

Once the tray 458 retracts into the incubator assembly 460, the tray remains stationary during illumination and read out. For a readout of the microtiter plate 456 to occur, the collimator assembly 708 generates an illumination pattern that is incident along the bottom surface 459 of the plate 456. Preferably, the instrument 100 generates a beam of light that is incident along an entire row of wells of the plate 456.

Alternatively, the instrument 100 generates a plurality of illumination beams that are simultaneously incident on a plurality of plate wells. The illumination pattern, comprising multiple beams, is generated by dual illumination fiber optic probes contained within the collimator assembly 708. The construction of the probes is as shown in FIG. 3. As previously herein described, the light reflected off of the biosensor surface may then be detected by the same plurality of probes contained within a collimator assembly 708. This reflected light is then analyzed via the spectrometer system 590.

Figure 11:
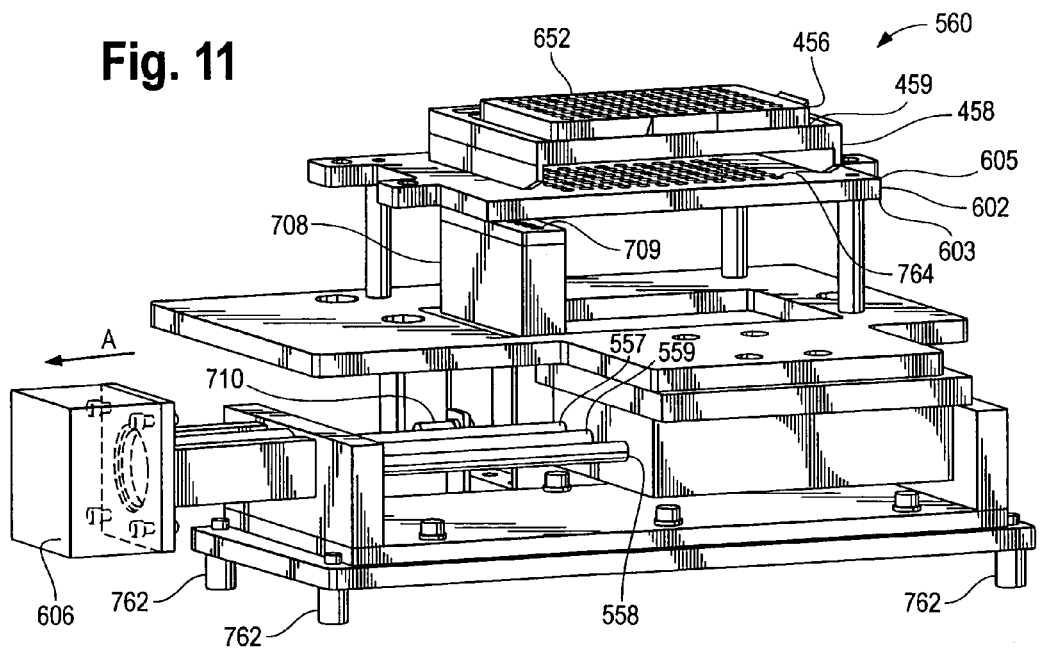

The incubator assembly 460 is provided with a plurality of apertures 764 along a bottom incubator assembly structure. As can be seen in FIG. 11, incubator assembly apertures 764 are conFigured to generally line-up and match the well locations 657 on the plate 456 when the plate 456 is in a readout position within the incubator assembly 460. For example, if there are 96 wells on the microwell well plate 456, the incubator assembly bottom portion 602 will be provided with 96 apertures 764. These apertures will be configured in the same type of array as the wells of the well plate (e.g., 8 rows by 12 columns). These apertures 764 provide clearance for light generated by collimator assembly 708 to reach the wells from the illuminating probes 709.

To enable user access to the tray and to the plate, the plate tray 458 extends out of the measuring apparatus 400. The tray 458 can be retracted into the apparatus 400 and the door cover 454 closed to begin microplate processing. Such processing could include mixing liquid in the microtiter wells, heating deposited liquids to a predetermined temperature, illumination of the microplate 456, and processing various reflected illumination patterns.

FIG. 9 illustrates a perspective view 580 of various internal components of the instrument 100 illustrated in FIG. 8. As shown in FIG. 9, internal components of the measuring instrument 580 include a transition stage assembly 560, heater controller unit 582, a controller board assembly 588, and a spectrometer unit 590. The transition stage assembly 560 includes the incubator assembly 460 and the collimator assembly 708. The heater controller unit 582, the controller board assembly 588, the transition stage assembly 560, and the spectrometer unit 590 are mounted on a base plate 592. The microplate well tray 456 is shown in the retracted position, outside of the incubator assembly 460.

The heater controller unit 582 provides temperature control to the incubator assembly 460. The controller board assembly 588 provides functional controls for the measuring apparatus including the mixing and other motion controls related to translation stage 560 and tray handling 458.

The spectrometer unit 590 contains an appropriate spectrometer for generating the PWV data. The design of the spectrometer will vary depending on the illumination source.

Figure 10:
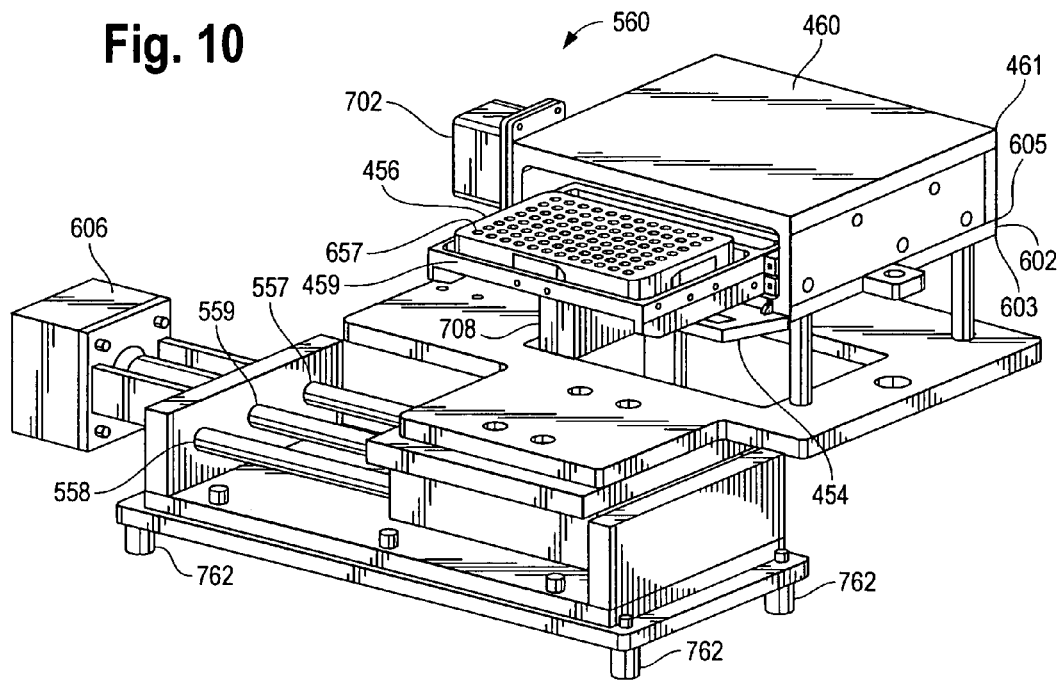

FIG. 10 illustrates a perspective view of the transition stage assembly 560 of the measuring instrument 400 illustrated in FIGS. 8 and 9. FIG. 11 illustrates the transition stage assembly 560 of FIG. 10 with an incubator assembly top portion 461 removed (See FIGS. 9 and 10). As can be seen from FIGS. 10 and 11, the transition stage assembly 560 includes the microwell tray 458 positioned in the retracted position. The microwell tray 458 has a plurality of wells 657, enters the incubation assembly 460 to initiate the read out process.

The microwell plate tray 458 is mounted on a top surface 605 of a bottom portion 602 of the incubator assembly 460. Preferably, where the microtiter tray 456 is a conventional microtiter tray having 96 wells, the bottom portion 602 of the incubator assembly 460 includes 96 holes. The microwell plate tray 458 is positioned over the bottom portion of the incubator assembly 602 such that the incubator assembly apparatus essentially matches up with the apertures (wells) contained in the microwell tray 458. Alternatively, the bottom portion 602 may contain a transparent section that matches the bottom portion of the plate.

During specimen illumination and measurement, the microwell tray 458 is preferably held in a stationary manner within the incubator assembly 460 by the bottom incubator assembly portion 602. During illumination and measurement, the collimator assembly 708 is held in a stationary manner while a stepping motor 606 drives the incubator assembly, including the plate, in a linear direction "A". As the incubator assembly 460 is driven along direction "A," the collimator assembly 708 illuminates the bottom surface 459 of microtiter plate 456. The resulting reflected illumination patterns are detected by the collimator assembly 708. A home position sensor 710 is provided as a portion of the translation stage assembly and to determine the position during the illumination process.

The transition stage assembly 760 is provided with a plurality of elastomer isolators 762. In this embodiment, a total of six elastomer isolators are used to provide isolation and noise reduction during illumination and read out.

As can be seen from FIGS. 10 and 11, the collimator assembly 708 is positioned below a bottom surface 603 of the incubator portion bottom portion 602. Preferably, the collimator assembly 708 includes a plurality of dual fiber probe heads 709. In the embodiment illustrated in FIG. 10, the collimator assembly 708 includes 8 dual fiber probe heads 709. These dual fiber probes could have a probe head configuration similar to the fiber optic probes as previously described.

For ease of explanation, only the bottom plate 602 of the incubator assembly 460 is shown is FIG. 11. The incubator assembly bottom portion 602 is provided with a plurality of apertures 764. Preferably, where the microwell plate 456 is provided with an 8×12 array of wells such as illustrated in FIG. 11, the incubator assembly bottom portion 602 will also include an 8×12 array of 96 apertures. These apertures will essentially match the 96 wells on the microwell plate 456. In this manner, the collimated white light generated by the collimator assembly 708 propagates through a first surface 603 along the incubator assembly bottom portion 602, and exit a second surface or top surface 605 of incubator assembly bottom portion 602. The collimated light can then illuminate a bottom well portion of the microwell plate 456. Alternately, bottom portion 602 may contain a transparent section that matches the bottom portion of the plate.

Referring to FIGS. 10 and 11, a drive motor 606 is provided for driving the incubator assembly during well scanning. A home position sensor 710 is provided as a stop measuring during the translation stage. The plate handling stage uses a stepping motor 702 to drive a rack-and-pinion mechanism to move the tray in and out of the door to the instrument. The scanning stage uses a stepping motor 606 to drive a leadscrew 559 along translation stage rails 557, 558 to provide relative motion between the microwell plate 456 and the collimator assembly 708.

A mixer assembly may be used for mixing the liquid in the wells. In the present invention, a mixing mechanism is located between the incubation chamber of the translation stage. Additionally, a mixing mechanism may be provided in an alternative location.

The grating surface of the sensor may be coated with compounds to enhance binding of target molecules in the sample, as described in the published application of Pepper et al., U.S. patent application Ser. No. 2003/0113766.

While presently preferred embodiments have been described with particularity, persons skilled in the art will appreciate that modifications to the disclosed embodiments are contemplated as being within the scope of the invention. The scope is to be determined by reference to the appended claims.

The invention claimed is:

1. A photonic crystal biosensor comprising:
   an array of two-dimensional unit cells, each of said unit cells having a substrate and a multitude of raised portions arranged in a regular repeating pattern wherein said raised portions are separated from each other by adjacent void portions, said raised portions made from a material having a relatively high index of refraction n1 greater than that of water;
   wherein each of said unit cells further comprises a defect wherein the regular repeating pattern of said raised portion separated by adjacent voids is modified such that at the defect said material having a relatively high index of refraction n1 occupies the space of one or more of the voids;
   wherein a localized maximum of electromagnetic field intensity is produced in the region of said defect in response to incident light on said photonic crystal at a resonant frequency;
   and wherein, during use, a fluid containing a sample to be tested is placed on said photonic crystal and contained in said void portions.

2. The photonic crystal biosensor of claim 1, further comprising a structure placed adjacent to said array of unit cells, said structure having a plurality of apertures, each of which overlie a plurality of said unit cells, and wherein said fluid sample introduced into said apertures in said structure is contained in said void portions proximate to the defect in said unit cells.

3. The photonic crystal biosensor of claim 2, wherein said structure comprises a multi-well device, arranged in an array or rows and columns of wells, which is affixed to said photonic crystal biosensor.

4. The photonic crystal biosensor of claim 1, wherein said multitude of raised portions comprise raised portions in said substrate and a material of index of refraction n1 deposited on said substrate.

5. The photonic crystal biosensor of claim 1, wherein said defects are located substantially at the center of each of said unit cells.

6. The photonic crystal biosensor of claim 1, wherein said material with an index of refraction n1 comprises a layer of between 100 and 140 nm high refractive index material with n1=2.25.

7. The photonic crystal biosensor of claim 1, further comprising a reading instrument illuminating said photonic crystal biosensor and determining a shift in the resonant frequency of the peak wavelength of light reflected from said photonic crystal biosensor.

8. The photonic crystal biosensor of claim 1, wherein the design of the defect is selected by use of a finite difference time domain computer model of said photonic crystal biosensor.

9. The photonic crystal biosensor of claim 1, wherein said array of unit cells comprises an array of unit cells, each comprising a two-dimensional array of raised portions and adjacent void portions forming a checkerboard arrangement.

10. The photonic crystal biosensor of claim 9, wherein the size of the raised portions and the size of the adjacent void portions are substantially equal except in the region of said defect.

11. The photonic crystal biosensor of claim 9, wherein the size of the raised portions and the size of the adjacent void portions varies continuously along an axis extending from the perimeter of said unit cell to the defect cavity at the center of the unit cell and to the opposite perimeter of said unit cell.

12. The photonic crystal biosensor of claim 1, wherein each of said unit cells comprises an arrangement of raised portions and adjacent void portions arranged in a hexagon, with the defect located at the center of the hexagon.

13. The photonic crystal biosensor of claim 12, wherein said void portions comprise an arrangement of holes formed in said substrate in a manner such that, in the periphery of said hexagon said holes are of a first size, and in the region of the center of said hexagon the holes are of a size smaller than said first size.

14. The photonic crystal biosensor of claim 13, wherein at the center of said hexagon, there is no hole.

15. A method of testing a sample, comprising the steps of:
1) introducing a fluid sample onto a defect cavity photonic crystal biosensor, said biosensor comprising an array of two-dimensional unit cells, each of said unit cells having a substrate and a multitude of raised portions arranged in a regular repeating pattern wherein said raised portions are separated from each other by adjacent void portions, said raised portions made from a material having a relatively high index of refraction n1 greater than that of water;
wherein each of said unit cells further comprises a defect wherein the regular repeating pattern of said raised portion separated by adjacent voids is modified such that at the defect said material having a relatively high index of refraction n1 occupies the space of one or more of the voids; wherein a localized maximum of electromagnetic field intensity is produced in the region of said defect in response to incident light on said photonic crystal at a resonant frequency;
2) illuminating said photonic crystal biosensor, and
3) determining the frequency of the peak wavelength of light either reflected from or transmitted through said photonic crystal biosensor.

16. The method of claim 15, wherein the photonic crystal biosensor is affixed to a device containing the fluid sample, said device arranged in an array of rows and columns.

17. The method of claim 15, wherein multitude of raised portions comprise raised portions in said substrate and a material of index of refraction n1 deposited on said substrate.

18. The method of claim 15, wherein said defects are located substantially at the center of each of said unit cells.

19. The method of claim 15, wherein said material with an index of refraction n1 comprises a layer of between 100 and 140 nm high refractive index material with n1=2.25.

* * * * *

UNITED STATES PATENT AND TRADEMARK OFFICE
CERTIFICATE OF CORRECTION

PATENT NO. : 6,990,259 B2  Page 1 of 1
APPLICATION NO. : 10/812635
DATED : January 24, 2006
INVENTOR(S) : Cunningham It is certified that error appears in the above-identified patent and that said Letters Patent is hereby corrected as shown below:

Col. 2, Line 65, "calorimetric" should read --colorimetric--.

Signed and Sealed this

Thirtieth Day of September, 2008

JON W. DUDAS
*Director of the United States Patent and Trademark Office*